United States Patent
Ashurst et al.

(10) Patent No.: US 6,511,652 B1
(45) Date of Patent: *Jan. 28, 2003

(54) METERED DOSE INHALER FOR BECLOMETHASONE DIPROPIONATE

(75) Inventors: Ian C. Ashurst, Ware (GB); Ignatius Loy Britto, Cary, NC (US); Craig Steven Herman, Raleigh, NC (US); Li Li-Bovet, Chapel Hill, NC (US); Michael Thomas Riebe, Raleigh, NC (US)

(73) Assignee: SmithKline Beecham Corp., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/506,834

(22) Filed: Feb. 18, 2000

Related U.S. Application Data

(63) Continuation of application No. 08/945,141, filed as application No. PCT/US96/05009 on Apr. 11, 1996, now Pat. No. 6,149,892.

(51) Int. Cl.$^7$ ................................................. A61K 9/12

(52) U.S. Cl. ........................ 424/45; 424/46; 128/200.14

(58) Field of Search ................. 424/45, 46; 128/203.15, 128/200.14

(56) References Cited

U.S. PATENT DOCUMENTS

| | | |
|---|---|---|
| 2,562,118 A | 7/1951 | Osdal |
| 2,721,010 A | 10/1955 | Meshberg |
| 2,886,217 A | 5/1959 | Thiel |
| 2,892,576 A | 6/1959 | Ward |
| 2,968,427 A | 1/1961 | Meshberg |
| 2,980,301 A | 4/1961 | de Gorter |
| 3,049,269 A | 8/1962 | Gawthrop |
| 3,052,382 A | 9/1962 | Gawthrop |
| 3,506,737 A | 4/1970 | Smith et al. |
| 3,611,990 A | 10/1971 | Paoletti et al. |
| 3,896,602 A | 7/1975 | Petterson |
| 3,929,537 A | 12/1975 | Erwin |
| 3,962,171 A | 6/1976 | Robbins |
| 4,087,026 A | 5/1978 | Petterson |
| 4,125,152 A | 11/1978 | Kestner et al. |
| 4,143,204 A | 3/1979 | Fang |
| 4,180,609 A | 12/1979 | Vassiliou |
| 4,335,121 A | 6/1982 | Phillips et al. |
| 4,339,483 A | 7/1982 | Ueno et al. |
| 4,407,481 A | 10/1983 | Bolton et al. |
| 4,423,823 A | 1/1984 | Franek et al. |
| 4,487,878 A | 12/1984 | Vasta |
| 4,626,157 A | 12/1986 | Franek et al. |
| 4,741,934 A | 5/1988 | Terayama et al. |
| 4,819,834 A | 4/1989 | Thiel |
| 4,826,132 A | 5/1989 | Moldenhauer |
| 4,861,647 A | 8/1989 | Ishikawa et al. |
| 4,897,439 A | 1/1990 | Rau et al. |
| 4,902,318 A | 2/1990 | Stevens et al. |
| 4,945,008 A | 7/1990 | Heyes et al. |
| 4,961,966 A | 10/1990 | Stevens et al. |
| 4,969,577 A | 11/1990 | Werding |
| 4,972,037 A | 11/1990 | Garbe et al. |
| 4,980,210 A | 12/1990 | Heyes |
| 4,992,474 A | 2/1991 | Skidmore et al. |
| 5,006,383 A | 4/1991 | Achille et al. |
| 5,043,191 A | 8/1991 | Endres et al. |
| 5,061,140 A | 10/1991 | Hamaguchi et al. |
| 5,168,107 A | 12/1992 | Tannenbaum |
| 5,176,132 A | 1/1993 | Drought et al. |
| 5,192,548 A | 3/1993 | Velasquez et al. |
| 5,202,110 A | 4/1993 | Dalby et al. |
| 5,208,226 A | 5/1993 | Palmer |
| 5,221,576 A | 6/1993 | Bosc et al. |
| 5,225,183 A * | 7/1993 | Purewal et al. |
| 5,250,356 A | 10/1993 | Batzar |
| 5,261,538 A * | 11/1993 | Evans |
| 5,270,305 A | 12/1993 | Palmer |
| 5,340,463 A | 8/1994 | Layre et al. |
| 5,345,980 A | 9/1994 | Burt et al. |
| 5,376,359 A | 12/1994 | Johnson |
| 5,411,771 A | 5/1995 | Tsai |
| 5,421,492 A | 6/1995 | Barger et al. |
| 5,447,600 A | 9/1995 | Webb |
| 5,468,798 A | 11/1995 | Leech |
| 5,503,144 A | 4/1996 | Bacon |
| 5,508,023 A | 4/1996 | Byron et al. |

(List continued on next page.)

FOREIGN PATENT DOCUMENTS

| | | |
|---|---|---|
| AU | B012188 | 9/1992 |
| CA | 2130867 | 8/1994 |
| DE | 2252754 | 10/1972 |

(List continued on next page.)

OTHER PUBLICATIONS

Dieter Köhler, "Systemic Therapy with Aerosols." In F. Morén, et al. (eds.), *Aerosols in Medicine: Principles, Diagnosis and Therapy* (Elsevier, 1993), ch. 12, pp. 303–319.

"PTFE als Mittel zur Verhinderung der Adhäsion." In Manfred Reiher and Hans Scheurlen (eds.), *Kunststoff–Handbuch* (Carl Hanser Verlag, 1971), Bd. XI, sec. 4.3.6.2, pp. 362–363.

(List continued on next page.)

*Primary Examiner*—Jose' G. Dees
*Assistant Examiner*—M. Haghighatian
(74) *Attorney, Agent, or Firm*—Birch, Stewart, Kolasch & Birch, LLP

(57) ABSTRACT

A metered dose inhaler having part or all of its internal surfaces coated with one or more fluorocarbon polymers, optionally in combination with one or more non-fluorocarbon polymers, for dispensing an inhalation drug formulation comprising beclomethasone dipropionate or a physiologically acceptable solvate thereof, and a fluorocarbon propellant, optionally in combination with one or more other pharmacologically active agents or one or more excipients.

25 Claims, No Drawings

U.S. PATENT DOCUMENTS

| | | | |
|---|---|---|---|
| 5,536,583 A | 7/1996 | Roberts et al. | |
| 5,597,433 A | 1/1997 | Dyble et al. | |
| 5,605,674 A | 2/1997 | Purewall et al. | |
| 5,674,472 A | 10/1997 | Akehurst et al. | |
| 5,674,473 A | 10/1997 | Purewal et al. | |
| 5,674,592 A | 10/1997 | Clark et al. | |
| 5,676,929 A | 10/1997 | Akehurst et al. | |
| 5,681,545 A | 10/1997 | Purewal et al. | |
| 5,683,676 A | 11/1997 | Akehurst et al. | |
| 5,683,677 A | 11/1997 | Purewal et al. | |
| 5,695,743 A | 12/1997 | Purewal et al. | |
| 5,720,940 A | 2/1998 | Purewal et al. | |
| 5,736,124 A * | 4/1998 | Akehurst et al. | |
| 5,891,420 A * | 4/1999 | Cutie | |
| 6,131,566 A * | 10/2000 | Ashurst et al. | 128/200.14 |
| 6,143,277 A * | 11/2000 | Ashurst et al. | |
| 6,149,892 A * | 11/2000 | Britto | |
| 6,253,762 B1 * | 7/2001 | Britto | 128/200.14 |

FOREIGN PATENT DOCUMENTS

| | | |
|---|---|---|
| DE | 2252754 A | 5/1973 |
| DE | 2227142 A | 12/1973 |
| DE | 3619926 | 6/1986 |
| DE | 3619926 A1 | 1/1987 |
| DE | 4009397 | 3/1990 |
| DE | 4023909 | 7/1990 |
| DE | 4124730 C2 | 1/1993 |
| DE | 4434425 | 3/1996 |
| DE | 19500726 | 7/1996 |
| EP | 0273980 | 7/1988 |
| EP | 0297712 | 1/1989 |
| EP | 0317865 | 5/1989 |
| EP | 0335315 A1 | 10/1989 |
| EP | 0338670 A2 | 10/1989 |
| EP | 0343015 | 11/1989 |
| EP | 0372777 | 6/1990 |
| EP | 0384606 | 8/1990 |
| EP | 0455463 | 11/1991 |
| EP | 0465741 | 1/1992 |
| EP | 0487200 | 5/1992 |
| EP | 0499142 | 8/1992 |
| EP | 0504112 A2 | 9/1992 |
| EP | 0561981 B1 | 9/1993 |
| EP | 0561987 B1 | 9/1993 |
| EP | 0607934 | 7/1994 |
| EP | 0609453 | 8/1994 |
| EP | 0642992 | 3/1995 |
| EP | 0561987 | 7/1995 |
| EP | 0561981 | 1/1996 |
| FR | 2267496 A | 11/1975 |
| FR | 2713299 | 6/1995 |
| GB | 1322084 | 3/1970 |
| GB | 1191700 | 5/1970 |
| GB | 1362495 | 8/1971 |
| GB | 1394327 | 5/1975 |
| GB | 1392192 | 4/1976 |
| GB | 1588463 | 8/1976 |
| GB | 2003415 | 8/1978 |
| GB | 2105189 | 3/1983 |
| GB | 2214891 | 9/1989 |
| GB | 2216794 | 10/1989 |
| HU | 0168483 | 5/1976 |
| HU | 0196303 | 11/1988 |
| HU | 0196904 | 2/1989 |
| HU | 0208398 | 10/1993 |
| HU | 0209609 | 5/1994 |
| JP | 01009158 | 1/1989 |
| JP | 01214433 | 8/1989 |
| JP | 02067374 | 3/1990 |
| JP | 03093525 | 4/1991 |
| JP | 04353442 | 12/1992 |
| JP | 06142799 | 5/1994 |
| RU | 2008939 | 3/1994 |
| RU | 2012362 | 5/1994 |
| RU | 2027448 | 1/1995 |
| WO | WO8101375 | 5/1981 |
| WO | 8604233 | 7/1986 |
| WO | 9104011 A1 | 4/1991 |
| WO | 9110606 | 7/1991 |
| WO | WO9208446 | 5/1992 |
| WO | 9211190 | 7/1992 |
| WO | 9220391 | 11/1992 |
| WO | 9311743 | 6/1993 |
| WO | 9311744 A1 | 6/1993 |
| WO | 9311745 A1 | 6/1993 |
| WO | WO9403153 | 2/1994 |
| WO | 9400921 | 6/1994 |
| WO | 9422722 | 10/1994 |
| WO | 9609816 | 4/1996 |
| WO | 9632099 | 10/1996 |
| WO | 9632150 | 10/1996 |
| WO | 9632151 | 10/1996 |
| WO | 9632345 | 10/1996 |
| WO | 9830262 | 7/1998 |

OTHER PUBLICATIONS

Subhash V. Gangal, "Tetrafluoroethylene Polymers." In *Encyclopedia of Polymer Science and Engineering* (J. Wiley, 1989), vol. 16, pp. 577–642.

Richard L. Johnson, "Fluorine Compounds, Organic." In *Kirk–Othmer Encyclopedia of Chemical Technology*, 3d ed. (J. Wiley, 1980), vol. 11, pp. 1–49.

"ICI Aims for 134a Lead," *Chemistry and Industry* (June 6, 1988), p. 347.

John J. Sciarra and Anthony J. Cutie, "Pharmaceutical Aerosols." In Leon Lachman, et al. (eds.), *The Theory and Practice of Industrial Pharmacy* (Lea & Febiger, 1986), ch. 20, pp. 589–618.

G. Bukton, *International J. Pharm.*, 83, 163–170 (1992).

*Journal of Teflon*, 4, pp. 1 and 4–6 (1963).

*Journal of Teflon*, 1, pp. 1 and 7 (1960).

Byron, Respiratory Drug Delivery, CRC Press, Inc., fl, 167–201 (1990).

Budavari, The Merck Index, Eleventh Ed., Merck & Co., Inc., pp. 37, 158–159 and 663–664 (1989).

Henry, The British Medical Assoc. Guide to Medicines & Drugs, Dorling Kindersely, London, p. 137 (1992).

R. Dalby et al., *Pharmaceutical Technology*, pp. 26–33, Mar. 1990.

A. R. Gennaro, *Remington's Pharmaceutical Sciences*, Mack Publishing Co., Inc., pp. 1670–1677 (1985).

A. R. Gennaro, *Remington's Pharmaceutical Sciences*, Mack Publishing Co., Inc., pp. 1670–1677 (1985).

Fundamentals of Polymer Adhesion, Chapter VIII, "Adhesion of Polymers to Substrates of an Inorganic Nature", pp. 289–230, 1974 (with English Translation).

* cited by examiner

METERED DOSE INHALER FOR BECLOMETHASONE DIPROPIONATE

This application is a continuation of U.S. application Ser No. 08/945,141, now U.S. Pat. No. 6,149,892 which was filed pursuant to 35 U.S.C. §371 as a United States National Phase Application of International Application No. PCT/US96/05009 filed Apr. 11, 1996, which claims priority from U.S. application Ser. No. 08/422,280, filed Apr. 14, 1995. The entire contents of each of the above-identified applications are hereby incorporated by reference.

BACKGROUND OF THE INVENTION

Drugs for treating respiratory and nasal disorders are frequently administered in aerosol formulations through the mouth or nose. One widely used method for dispensing such aerosol drug formulations involves making a suspension formulation of the drug as a finely divided powder in a liquefied gas known as a propellant. The suspension is stored in a sealed container capable of withstanding the pressure required to maintain the propellant as a liquid. The suspension is dispersed by activation of a dose metering valve affixed to the container.

A metering valve may be designed to consistently release a fixed, predetermined mass of the drug formulation upon each activation. As the suspension is forced from the container through the dose metering valve by the high vapor pressure of the propellant, the propellant rapidly vaporizes leaving a fast moving cloud of very fine particles of the drug formulation. This cloud of particles is directed into the nose or mouth of the patient by a channelling device such as a cylinder or open ended cone. Concurrently with the activation of the aerosol dose metering valve, the patient inhales the drug particles into the lungs or nasal cavity. Systems of dispensing drugs in this way are known as "metered dose inhalers" (MDI's). See Peter Byron, *Respiratory Drug Delivery,* CRC Press, Boca Raton, Fla. (1990) for a general background on this form of therapy.

Patients often rely on medication delivered by MDI's for rapid treatment of respiratory disorders which are debilitating and in some cases, even life threatening. Therefore, it is essential that the prescribed dose of aerosol medication delivered to the patient consistently meet the specifications claimed by the manufacturer and comply with the requirements of the FDA and other regulatory authorities. That is, every dose in the can must be the same within close tolerances.

Some aerosol drugs tend to adhere to the inner surfaces, i.e., walls of the can, valves, and caps, of the MDI. This can lead to the patient getting significantly less than the prescribed amount of drug upon each activation of the MDI. The problem is particularly acute with hydrofluoroalkane (also known as simply "fluorocarbon" propellant systems, e.g., P134a and P227, under development in recent years to replace chlorofluorocarbons such as P11, P114, and P12.

We have found that coating the interior can surfaces of MDI's with a fluorocarbon polymer significantly reduces or essentially eliminates the problem of drug adhesion or deposition on the can walls and thus ensures consistent delivery of medication in aerosol form from the MDI.

SUMMARY OF THE INVENTION

A metered dose inhaler having part or all of its internal metallic surfaces coated with one or more fluorocarbon polymers, optionally in combination with one or more non-fluorocarbon polymers, for dispensing an inhalation drug formulation comprising beclomethasone dipropionate or a physiologically acceptable solvate thereof, and a fluorocarbon propellant, optionally in combination with one or more other pharmacologically active agents or one or more excipients.

DETAILED DESCRIPTION OF THE INVENTION

The term "metered dose inhaler" or "MDI" means a unit comprising a can, a crimped cap covering the mouth of the can, and a drug metering valve situated in the cap, while the term "MDI system" also includes a suitable channelling device. The terms "MDI can" means the container without the cap and valve. The term "drug metering valve" or "MDI valve" refers to a valve and its associated mechanisms which delivers a predetermined amount of drug formulation from an MDI upon each activation. The channelling device may comprise, for example, an actuating device for the valve and a cylindrical or cone-like passage through which medicament may be delivered from the filled MDI can via the MDI valve to the nose or mouth of a patient, e.g. a mouthpiece actuator. The relation of the parts of a typical MDI is illustrated in U.S. Pat. No. 5,261,538 incorporated herein by reference.

U.S. Pat. No. 3,312,590, incorporated herein by reference, teaches an antiinflammatory steroid compound know by the chemical name 9-chloro-1 1D, 17, 21-trihydroxy-16fi-methylprergna-1,4-diene-3, 20-dione 17, 21-dipropionate and the generic name "beclomethasone dipropionate". Beclomethasone dipropionate in aerosol form, has been accepted by the medical community as useful in the treatment of asthma and is marketed under the trademarks "Beclovent", "Becotide", and "Beconase".

The term "drug formulation" means beclomethasone dipropionate (or a physiologically acceptable solvate thereof) optionally in combination with one or more other pharmacologically active agents such as other antiinflammatory agents, analgesic agents or other respiratory drugs and optionally containing one or more excipients. The term "excipients" as used herein mean chemical agents having little or no pharmacological activity (for the quantities used) but which enhance the drug formulation or the performance of the MDI system. For example, excipients include but are not limited to surfactants, preservatives, flavorings, antioxidants, antiaggregating agents, and cosolvents, e.g., ethanol and diethyl ether.

Suitable surfactants are generally known in the art, for example, those surfactants disclosed in European Patent Application No. 0327777. The amount of surfactant employed is desirable in the range of 0.0001% to 50% weight to weight ratio relative to the drug, in particular, 0.05 to 5% weight to weight ratio. A particularly useful surfactant is 1,2-di[7-(F-hexyl)hexanoyl]-glycero-3-phospho-N,N,N-trimethylethanolamine also know as 3,5,9-trioxa-4-phosphadocosan-1-aminium, 17,17,18,18,19,19,20,20,21, 21,22,22,22-tridecafluoro-7-[(8,8,9,9,10,10,11,11,12,12,13, 13,13-tridecafluoro-1-oxotridecyl)oxy]-4-hydroxy-N,N,N-trimethyl-10oxo-, inner salt,4-oxide.

A polar cosolvent such as $C_{2-6}$ aliphatic alcohols and polyols eg ethanol, isopropanol and propylene glycol, and preferably ethanol, may be included in the drug formulation in the desired amount, either as the only excipient or in addition to other excipients such as surfactants. Suitably, the drug formulation may contain 0.01 to 5% w/w based on the propellant of a polar cosolvent eg ethanol, preferably 0.1 to 5% w/w e.g. 0.1 to 1% w/w.

It will be appreciated by those skilled in the art that the drug formulation for use in the invention may, if desired, contain beclomethasone dipropionate (or a physiologically acceptable solvate thereof) in combination with one or more other pharmacologically active agents. Such medicaments may be selected from any suitable drug useful in inhalation therapy. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; anti-inflammatories, e.g. fluticasone (e.g. the propionate), flunisolide, budesonide, tipredane or triamcinolone acetonide; antitussives, e.g. noscapine; bronchodilators, e.g. salbutamol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, or (-)-4-amino-3,5-dichloro-α-[[[6-[2-(2-pyridinyl)ethoxy]hexyl]amino]methyl] benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant.

Particularly preferred drug formulations contain beclomethasone dipropionate (or a physiologically acceptable solvate thereof) in combination with a bronchodilator such as salbutamol (e.g. as the free base or the sulphate salt) or salmeterol (e.g. as the xinafoate salt).

"Propellants" used herein mean pharmacologically inert liquids with boiling points from about room temperature (25° C.) to about −25° C. which singly or in combination exert a high vapor pressure at room temperature. Upon activation of the MDI system, the high vapor pressure of the propellant in the MDI forces a metered amount of drug formulation out through the metering valve then the propellant very rapidly vaporizes dispersing the drug particles. The propellants used in the present invention are low boiling fluorocarbons; in particular, 1,1,1,2-tetrafluoroethane also known as "propellant 134a" or "P134a" and 1,1,1,2,3,3,3-heptafluoropropane also know as "propellant 227" or "P 227".

Drug formulations for use in the invention may be free or substantially free of formulation excipients e.g. surfactants and cosolvents etc. Such drug formulations are advantageous since they may be substantially taste and odour free, less irritant and less toxic than excipient-containing formulations. Thus, a preferred drug formulation consists essentially of beclomethasone dipropionate (or a physiologically acceptable solvate thereof), optionally in combination with one or more other pharmacologically active agents particularly salbutamol (or a physiologically acceptable salt thereof), and a fluorocarbon propellant. Preferred propellants are 1,1,1,2-tetrafluoroethane, 1,1,1,2,3,3,3-heptafluoro-n-propane or mixtures thereof, and especially 1,1,1,2-tetrafluoroethane.

Most often the MDI can and cap are made of aluminum or an alloy of aluminum, although other metals not affected by the drug formulation, such as stainless steel, an alloy of copper, or tin plate, may be used. An MDI can may also be fabricated from glass or plastic. Preferably, however, the MDI cans employed in the present invention are made of aluminium or an alloy thereof. Advantageously, strengthened aluminium or aluminum alloy MDI cans may be employed. Such strengthened MDI cans are capable of withstanding particularly stressful coating and curing conditions, e.g. particularly high temperatures, which may be required for certain fluorocarbon polymers. Strengthened MDI cans which have a reduced tendency to malform under high temperatures include MDI cans comprising side walls and a base of increased thickness and MDI cans comprising a substantially ellipsoidal base (which increases the angle between the side walls and the base of the can), rather than the hemispherical base of standard MDI cans. MDI cans having an ellipsoidal base offer the further advantage of facilitating the coating process.

The drug metering valve consists of parts usually made of stainless steel, a pharmacologically inert and propellant resistant polymer, such as acetal, polyamide (e.g., Nylon®), polycarbonate, polyester, fluorocarbon polymer (e.g., Teflon®) or a combination of these materials. Additionally, seals and "O" rings of various materials (e.g., nitrile rubbers, polyurethane, acetyl resin, fluorocarbon polymers), or other elastomeric materials are employed in and around the valve.

Fluorocarbon polymers for use in the invention include fluorocarbon polymers which are made of multiples of one or more of the following monomeric units: tetrafluoroethylene, (PTFE), fluorinated ethylene propylene (FEP), perfluoroalkoxyalkane (PFA), ethylene tetrafluoroethylene (ETFE), vinyldienefluoride (PVDF), and chlorinated ethylene tetrafluoroethylene. Fluorinated polymers which have a relatively high ratio of fluorine to carbon, such as perfluorocarbon polymers e.g. PTFE, PFA, and FEP, are preferred.

The fluorinated polymer may be blended with non-fluorinated polymers such as polyamides, polyimides, polyethersulfones, polyphenylene sulfides and amine-formaldehyde thermosetting resins. These added polymers improve adhesion of the polymer coating to the can walls. Preferred polymer blends are PTFE/FEP/polyamideimide, PTFE/polyethersulphone (PES) and FEP-benzoguanamine.

Particularly preferred coatings are pure PFA, FEP and blends of PTFE and polyethersulphone (PES).

Fluorocarbon polymers are marketed under trademarks such as Teflon®, Tefzel®, Halar®, Hostaflon®, (a copolymer prepared by copolymeizing TFE and perfluoropropyl vinyl ether) Polyflon® and Neoflon®. Grades of polymer include FEP DuPont 856-200, (a coplymer prepared by copolymerizing TFE and perfluoropropyl vinyl ether) PFA DuPont 857-200, PTFE-PES DuPont 3200-100, PTFE-FEP-polyamideimide DuPont 856P23485, FEP powder DuPont 532 and PFA Hoechst 6900n. The coating thickness is in the range of about 1 μm to about 1 mm. Suitably the coating thickness is in the range of about 1 μm to about 100 μm, e.g. 1 μm to 25 μm. Coatings may be applied in one or more coats.

Preferably the fluorocarbon polymers for use in the invention are coated onto MDI cans made of metal, especially MDI cans made of aluminium or an alloy thereof.

The particle size of the particular (e.g., micronised) drug should be such as to permit inhalation of substantially all the drug into the lungs upon administration of the aerosol formulation and will thus be less than 100 microns, desirably less than microns, and, in particular, in the range of 1–10 microns, e.g., 1–5 microns.

The final aerosol formulation desirably contains 0.005–10% weight to weight ratio, in particular 0.005–5% weight to weight ratio, especially 0.01–1.0% weight to weight ratio, of drug relative to the total weight of the formulation.

A further aspect of the present invention is a metered dose inhaler having part or all of its internal metallic surfaces coated with one or more fluorocarbon polymers, optionally in combination with one or more fluorocarbon polymers, for dispersing an inhalation drug formulation comprising beclomethasone dipropionate and a fluorocarbon propellant optionally in combination with one or more other pharmacologically active agents and one or more excipients.

A particular formulation for use in the metered dose inhaler of the present invention comprises:

(a) beclomethasone dipropionate monohydrate, the particle size of substantially all the monohydrate being less than 20 microns;

(b) at least 0.015% by weight of the formulation of water in addition to the water of crystallization associated with said monohydrate; and (c) a fluorocarbon propellant.

Such aerosol formulations desirably contain at least 0.015% (e.g., 0.015 to 0.1%) by weight of the formulation of water (excluding the water of crystallization associated with the beclomethasone dipropionate monohydrate), preferably at least 0.02%, for example 0.025% by weight or more of added water. Preferred formulations according to the invention contain at least 0.026%, for example 0.026 to 0.08% by weight of water, in addition to the water of crystallization associated with the beclomethasone dipropionate monohydrate. Optionally, a cosolvent such as ethanol may be included in the formulation in the desired amount. Suitably, the formulation may contain 0.05 to 3.0% w/w based on the propellant of a polar cosolvent such as ethanol. Preferably the fluorocarbon propellant is 1,1,1,2-tetrafluoroethane, 1,1,1,2,3,3,3-heptafluoro-n-propane or mixtures thereof, and especially 1,1,1,2-tetrafluoroethane.

Further drug formulations for use in the invention are free or substantially free of surfactants. Thus, a further formulation comprises or consists essentially of beclomethasone dipropionate or a physiologically acceptable solvate thereof, optionally in combination with one or more other pharmacologically active agents, a fluorocarbon propellant and 0.01 to 0.05% w/w based on the propellant of a polar cosolvent such as ethanol, which formulation is free of surfactant. Preferably the propellant is 1,1,1,2-tetrafluoroethane or 1,1,1,2,3,3,3-heptafluoro-n-propane, although mixtures thereof may also be used.

A particular aspect of the present invention is an MDI having part or essentially all of its internal surfaces e.g. metallic surfaces coated with PFA or FEP, or blended fluoropolymer resin systems such as PTFE-PES with or without a proper coat of polyamideimide or polyethersulfone for dispersing a drug formulation as defined hereinabove. Preferably the MDI can is made of aluminum or an alloy thereof.

The MDI can may be coated by the means known in the art of metal coating. For example, a metal, such as aluminum or stainless steel, may be precoated as coil stock and cured before being stamped or drawn into the can shape. This method is well is suited to high volume production for two reasons. First, the art of coating coil stock is well developed and several manufacturers can custom coat metal coil stock to high standards of uniformity and in a wide range of thicknesses. Second, the precoated stock can be stamped or drawn at high speeds and precision by essentially the same methods used to draw or stamp uncoated stock.

Other techniques for obtaining coated cans is by electrostatic dry powder coating or by spraying preformed MDI cans inside with formulations of the coating fluorinated polymer/polymer blend and then curing. The preformed MDI cans may also be dipped in the fluorocarbon polymer/polymer blend coating formulation and cured, thus becoming coated on the inside and out. The fluorocarbon polymer/polymer blend formulation may also be poured inside the MDI cans then drained out leaving the insides with the polymer coat. Conveniently, for ease of manufacture, preformed MDI cans are spray-coated with the fluorinated polymer/polymer blend.

The fluorocarbon polymer/polymer blend may also be formed in situ at the can walls using plasma polymerization of the fluorocarbon monomers. Fluorocarbon polymer film may be blown inside the MDI cans to form bags. A variety of fluorocarbon polymers such as ETFE, FEP, and PTFE are available as film stock.

The appropriate curing temperature is dependent on the fluorocarbon polymer/polymer blend chosen for the coating and the coating method employed. However, for coil coating and spray coating temperatures in excess of the melting point of the polymer are typically required, for example, about 50° C. above the melting point for up to about 20 minutes such as about 5 to 10 minutes eg about 8 minutes or as required. For the above named preferred and particularly preferred fluorocarbon polymer/polymer blends curing temperatures in the range of about 300° C. to about 400° C., e.g. about 350° C. to 380° C. are suitable. For plasma polymerization typically temperatures in the range of about 20° C. to about 100° C. may be employed.

The fluorocarbon polymer may also be formed in situ at the can walls using plasma polymerization of the fluorocarbon monomers. Fluorocarbon polymer film may be blown inside the MDI cans to form bags. A variety of fluorocarbon polymers such as ETFE, FEP, and PTFE are available as film stock.

The MDI's taught herein may be prepared by methods of the art (e.g., see Byron, above and U.S. Pat. No. 5,345,980) substituting conventional cans for those coated with a fluorinated polymer. That is, beclomethasone dipropionate and other components of the formulation are filled into an aerosol can coated with a fluorinated polymer. The can is fitted with a cap assembly which is crimped in place. The suspension of the drug in the fluorocarbon propellant in liquid form may be introduced through the metering valve as taught in U.S. Pat. No. 5,345,980 incorporated herein by reference.

The MDI's with fluorocarbon coated interiors taught herein may be used in medical practice in a similar manner as non-coated MDI's now in clinical use. However the MDI's taught herein are particularly useful for containing and dispensing inhaled drug formulations with hydrofluoroalkane fluorocarbon propellants such as 134a with little, or essentially no, excipient and which tend to deposit or cling to the interior walls and parts of the MDI system. In certain case it is advantageous to dispense an inhalation drug with essentially no excipient, e.g., where the patient may be allergic to an excipient or the drug reacts with an excipient.

MDI's containing the formulations described hereinabove, MDI systems and the use of such MDI systems for the treatment of respiratory disorders e.g. asthma comprise further aspects of the present invention.

It will be apparent to those skilled in the art that modifications to the invention described herein can readily be made without departing from the spirit of the invention. Protection is sought for all the subject matter described herein including any such modifications.

The following non-limitative Examples serve to illustrate the invention.

EXAMPLES

Example 1

Standard 12.5 mL MDI cans (Presspart Inc., Cary, N.C.) were spray-coated (Livingstone Coatings, Charlotte, N.C.) with primer (DuPont 851-204) and cured to the vendor's standard procedure, then further spray-coated with either FEP or PFA (DuPont 856-200 and 857-200, respectively) and cured according to the vendor's standard procedure. The thickness of the coating is approximately 10 $\mu$m to 50 $\mu$m. These cans are then purged of air (see PCT application number WO94/22722 (PCT/EP94/00921)), the valves crimped in place, and a suspension of about 24 mg beclomethasone dipropionate in about 18 gm P134a is filled through the valve.

Example 2

Standard 0.46 mm thick aluminum sheet (United Aluminum) was spray-coated (DuPont, Wilmington, Del.) with FEP (DuPont 856-200) and cured. This sheet was then deep-drawn into cans (Presspart Inc., Cary, N.C.). The thickness of the coating is approximately 10 $\mu$m to 50 $\mu$m. These cans are then purged of air, the valves crimped in place, and a suspension of about 60 mg beclomethasone dipropionate in about 18 gm P134A is filled through the valve.

Example 3

Standard 12.5 ml MDI cans (Presspart Inc., Cary N.C.) are spray-coated with PTFE-PES blend (DuPont) as a single coat and cured according to the vendor's standard procedure. The thickness of the coating is between approximately 1 $\mu$m and approximately 20 $\mu$m. These cans are then purged of air, the valves crimped in place, and a suspension of about 68 mg micronised beclomethasone dipropionate monohydrate in about 6.1 mg water and about 18.2 g P134a is filled through the valve.

Example 4

Standard 12.5 ml MDI cans (Presspart Inc., Cary N.C.) are spray-coated with PTFE-FEP-polyamideimide blend (DuPont) and cured according to the vendor's standard procedure. The thickness of the coating is between approximately 1 $\mu$m and approximately 20 $\mu$m. These cans are then purged of air the valves crimped in place, and a suspension of about 68 mg micronised beclomethasone dipropionate monohydrate in about 6.1 mg water and about 18.2 g P134a is filled through the valve.

Example 5

Standard 12.5 ml MDI cans (Presspart Inc., Cary N.C.) are spray-coated with FEP powder (DuPont FEP 532) using an electrostatic gun. The thickness of the coating is between approximately 1 $\mu$m and approximately 20 $\mu$m. These cans are then purged of air, the valves crimped in place, and a suspension of about 68 mg micronised beclomethasone dipropionate monohydrate in about 6.1 mg water and about 18.2 g P134a is filled through the valve.

Example 6

Standard 0.46 mm thick aluminium sheet is spray coated with FEP-Benzoguanamine and cured. This sheet is then deep-drawn into cans. These cans are then purged of air, the valves crimped in place, and a suspension of about 68 mg micronised beclomethasone dipropionate monohydrate in about 6.1 mg water and about 18.2 g P134a is filled through the valve.

Example 7

Standard 2.5 ml MDI cans (Presspart Inc., Cary N.C.) are spray-coated with an aqueous dispersion of PFA (Hoechst PFA-6900n) and cured. The thickness of the coating is between approximately 1 $\mu$m and approximately 20 $\mu$m. These cans are then purged of air, the valves crimped in place, and a suspension of about 68 mg micronised beclomethasone dipropionate monohydrate in about 6.1 mg water and about 18.2 g P134a is filled through the valve.

Example 8

Standard 12.5 ml MDI cans (Presspart Inc., Cary N.C.) are spray-coated with PTFE-PES blend (DuPont) as a single coat and cured according to the vendor's standard procedure. The thickness of the coating is between approximately 1 $\mu$m and approximately 20 $\mu$m. These cans are then purged of air, the valves crimped in place, and about 68 mg micronised beclomethasone dipropionate monohydrate in about 182 mg ethanol and about 18.2 g P134a is filled through the valve.

Example 9

Standard 12.5 ml MDI cans (Presspart Inc., Cary N.C.) are spray-coated with PTFE-FEP-polyamideimide blend (DuPont) and cured according to the vendor's standard procedure. The thickness of the coating is between approximately 1 $\mu$m and approximately 20 $\mu$m. These cans are then purged of air the valves crimped in place, and about 68 mg micronised beclomethasone dipropionate monohydrate in about 182 mg ethanol and about 18.2 g P134a is filled through the valve.

Example 10

Standard 12.5 ml MDI cans (Presspart Inc., Cary N.C.) are spray-coated with FEP powder (DuPont FEP 532) using an electrostatic gun. The thickness of the coating is between approximately 1 $\mu$m and approximately 20 $\mu$m. These cans are then purged of air, the valves crimped in place, and about 68 mg micronised beclomethasone dipropionate monohydrate in about 182 mg ethanol and about 18.2 g P134a is filled through the valve.

Example 11

Standard 0.46 mm thick aluminium sheet is spray coated with FEP-Benzoguanamine and cured. This sheet is then deep-drawn into cans. These cans are then purged of air, the valves crimped in place, and about 68 mg micronised beclomethasone dipropionate monohydrate in about 182 mg ethanol and about 18.2 g P134a is filled through the valve.

Example 12

Standard 12.5 ml MDI cans (Presspart Inc., Cary N.C.) are spray-coated with an aqueous dispersion of PFA (Hoechst PFA-6900n) and cured. The thickness of the coating is between approximately 1 $\mu$m and approximately 20 $\mu$m. These cans are then purged of air, the valves crimped in place, and about 68 mg micronised beclomethasone dipropionate monohydrate in about 182 mg ethanol and about 18.2 g P134a is filled through the valve.

Example 13

Standard 12.5 ml MDI cans (Presspart Inc., Cary N.C.) are spray-coated with PTFE-PES blend (DuPont) as a single coat and cured according to the vendor's standard procedure. The thickness of the coating is between approximately 1 μm and approximately 20 μm. These cans are then purged of air, the valves crimped in place, and about 13.6 mg micronised beclomethasone dipropionate in about 107 mg ethanol and about 21.4 g P227 is filled through the valve.

Example 14

Standard 12.5 ml MDI cans (Presspart Inc., Cary N.C.) are spray-coated with PTFE-FEP-polyamideimide blend (DuPont) and cured according to the vendor's standard procedure. The thickness of the coating is between approximately 1 μm and approximately 20 μm. These cans are then purged of air the valves crimped in place, and about 13.6 mg micronised beclomethasone dipropionate in about 107 mg ethanol and about 21.4 g P227 is filled through the valve.

Example 15

Standard 12.5 ml MDI cans (Presspart Inc., Cary N.C.) are spray-coated with FEP powder (DuPont FEP 532) using an electrostatic gun. The thickness of the coating is between approximately 1 μm and approximately 20 μm. These cans are then purged of air, the valves crimped in place, and about 13.6 mg micronised beclomethasone dipropionate in about 107 mg ethanol and about 21.4 g P227 is filled through the valve.

Example 16

Standard 0.46 mm thick aluminium sheet is spray coated with FEP-Benzoguanamine and cured. This sheet is then deep-drawn into cans. These cans are then purged of air, the valves crimped in place, and about 13.6 mg micronised beclomethasone dipropionate in about 107 mg ethanol and about 21.4 g P227 is filled through the valve.

Example 17

Standard 12.5 ml MDI cans (Presspart Inc., Cary N.C.) are spray-coated with an aqueous dispersion of PFA (Hoechst PFA-6900n) and cured. The thickness of the coating is between approximately 1 μm and approximately 20 gm. These cans are then purged of air, the valves crimped in place, and about 13.6 mg micronised beclomethasone dipropionate in about 107 mg ethanol and about 21.4 g P227 is filled through the valve.

Examples 18–22

Examples 3 to 7 are repeated except that about 24 mg salbutamol as the free base or equivalent weight of salt e.g. sulphate with about 12 mg beclomethasone dipropionate monohydrate in about 364 mg ethanol and about 18.2 g P134a is filled through the valve.

Examples 23–42

Examples 3 to 22 are repeated except that modified 12.5 ml MDI cans having a substantially ellipsoidal base (Presspart Inc., Cary N.C.) are used.

Dose delivery from the MDIs tested under simulated use conditions is found to be constant, compared to control MDIs filled into uncoated cans which exhibit a significant decrease in dose delivered through use.

We claim:

1. A metered dose inhaler, comprising:
    a can having a mouth and an internal surface wherein part or all of said internal surface is coated with a polymer comprising one or more fluorocarbon polymers, wherein said fluorocarbon polymer comprises monomeric units made from one or more monomers selected from the group consisting of tetrafluoroethylene, hexafluoropropylene, perfluoroalkoxyalkylene, and vinylidene fluoride;
    a cap covering said mouth of said can in communication with a drug metering valve; and
    an inhalation medicament formulation, consisting essentially of a medicament formulated with a fluorocarbon propellant, wherein the fluorocarbon propellant is 1,1,1,2-tetrafluoroethane or 1,1,1,2,3,3,3-heptafluoro-n-propane or combinations thereof, and optionally one or more excipients selected from the group consisting of preservative, flavoring, antioxidant, antiaggregating agent, ethanol and diethyl ether.

2. The metered dose inhaler according to claim 1, wherein the fluorocarbon propellant is 1,1,1,2-tetrafluoroethane.

3. The metered dose inhaler according to claim 1, wherein said one or more fluorocarbon polymers is a perfluorocarbon polymer.

4. The metered dose inhaler according to claim 1, wherein said one or more fluorocarbon polymers is selected from the group consisting of polytetrafluoroethylene, perfluoroalkoxyalkylene, and perfluorinated ethylene propylene copolymer.

5. The metered dose inhaler according to claim 1, wherein said perfluorocarbon polymer is made from monomeric units comprising perfluorinated ethylene propylene.

6. The metered dose inhaler according to claim 1, wherein said medicament formulation comprises 0.01 to 5% w/w of ethanol based on the weight of propellant.

7. The metered dose inhaler according to claim 1, wherein the medicament formulation comprises ethanol.

8. The metered dose inhaler according to claim 1, wherein the medicament formulation contains a medicament formulated with said fluorocarbon propellant and 0.01 to 5 w/w of ethanol or diethyl ether based on the propellant, said medicament formulation being substantially free of surfactant.

9. The metered dose inhaler according to claim 1, comprising a can made of metal wherein part or all of the internal metallic surface are coated with said polymer composition.

10. The inhaler according to claim 9, wherein the metal is aluminum or an alloy thereof.

11. A metered dose inhaler system comprising the metered dose according to claim 1 fitted into a suitable channeling device for oral or nasal inhalation of a formulated medicament.

12. The metered dose inhaler according to claim 1, wherein said one or more fluorocarbon polymers is polytetrafluoroethylene.

13. The metered dose inhaler according to claim 1, wherein said more fluorocarbon polymers is made from monomeric units comprising polyfluoroalkoxyalkylene.

14. The metered dose inhaler according to claim 1, wherein said one or more fluorocarbon polymers comprises perfluorinated ethylene propylene, which is coated on an aluminum can.

15. The metered dose inhaler according to claim 1, wherein the thickness of said coating is 1 μm to 1 mm.

16. The metered dose inhaler according to claim 1, wherein the thickness of said coating is 1 μm to 100 μm.

17. The metered dose inhaler according to claim 1, wherein the thickness of said coating is 1 μm to 25 μm.

18. The inhaler according to claim 9, wherein said coating is applied to said internal surface of a preformed can.

19. The inhaler according to claim 9, wherein said coating is applied by spray coating said polymer.

20. The inhaler according to claim 9, wherein said coating is applied by spray coating said polymer on the internal metallic surface of said can and curing said coating after it is sprayed.

21. The metered dose inhaler of claim 1, said medicament comprising beclomethasone dipropionate.

22. A metered dose inhaler, comprising:
a can having part or all of its internal surfaces coated with a polymer comprising one or more fluorocarbon polymers, wherein said fluorocarbon polymer comprises monomeric units made from one or more monomers selected from the group consisting of tetrafluoroethylene, hexafluoropropylene, perfluoroalkoxyalkylene, and vinylidene fluoride;
a cap in communication with a means for metering an inhalation medicament; and
an inhalation medicament formulation, consisting essentially of a medicament formulated with a fluorocarbon propellant, wherein the fluorocarbon propellant is 1,1,1,2-tetrafluoroethane or 1,1,1,2,3,3,3-heptafluoro-n-propane or combinations thereof, and optionally one or more excipients selected from the group consisting of preservative, flavoring, antioxidant, antiaggregating agent, ethanol and diethyl ether.

23. A metered dose inhaler system, comprising:
a metered dose inhaler comprising,
a can having a mouth, said can having part or all of its internal surfaces coated with a polymer blend comprising (i) one or more fluorocarbon polymers comprising monomeric units made from one or more monomers selected from the group consisting of tetrafluoroethylene, hexafluoropropylene, perfluoroalkoxyalkylene, and vinylidene fluoride in combination with (ii) one or more nonfluorocarbon polymers selected from the group consisting of a polyamide, a polyimide, a polyamideimide, a polyethersulphone, a polyphenylene sulfide and an amine-formaldehyde thermosetting resin;
a cap in communication with the mouth of the can, the cap containing a drug metering valve capable of metering an inhalation medicament formulation; and
an inhalation medicament formulation, comprising 0.005 to 10% by weight of beclomethasone dipropionate or a physiological acceptable solvate thereof relative to the total weight of said inhalation medicament formulation formulated with a fluorocarbon propellant, said fluorocarbon propellant is selected from the group consisting of 1,1,1,2-tetrafluoroethane or 1,1,1,2,3,3,3-heptafluoron-n-propane and combinations thereof; and
a channeling device in communication with said metered dose inhaler, said channeling device comprising an actuating device for the valve and a cylindrical or cone shaped passage through which medicament is delivered from the metered dose inhaler.

24. A medicament delivery product, comprising:
a metered dose inhaler having internal metallic surfaces, wherein part or all of said metallic internal surfaces are coated with a polymer comprising one or more fluorocarbon polymers, wherein said fluorocarbon polymer comprises monomeric units made from one or more monomers selected from the group consisting of tetrafluoroethylene, hexafluoropropylene, perfluoroalkoxyalkylene, and vinylidene fluoride; and
an inhalation medicament formulation contained in said metered dose inhaler, said inhalation medicament formulation consisting essentially of a medicament formulated with a fluorocarbon propellant, wherein the fluorocarbon propellant is 1,1,1,2-tetrafluoroethane or 1,1,1,2,3,3,3-heptafluoro-n-propane or combinations thereof, and optionally one or more excipients selected from the group consisting of preservative, flavoring, antioxidant, antiaggregating agent, ethanol and diethyl ether.

25. The product according to claim 24, wherein said internal metallic surfaces are part of a drug metering valve.

* * * * *

UNITED STATES PATENT AND TRADEMARK OFFICE
CERTIFICATE OF CORRECTION

PATENT NO. : 6,511,652 B1
DATED : January 28, 2003
INVENTOR(S) : Ashurst, Ian C.

It is certified that error appears in the above-identified patent and that said Letters Patent is hereby corrected as shown below:

<u>Title page,</u>
Item [54], "METERED DOSE INHALER FOR BECLOMETHASONE DIPROPIONATE" should read -- METERED DOSE INHALER HAVING AN INTERNAL SURFACE COATED WITH FLUOROCARBON POLYMER --

<u>Column 12,</u>
Line 6, "pysiological acceptable" should read -- pysiologically acceptable --

Signed and Sealed this

Eighteenth Day of November, 2003

JAMES E. ROGAN
*Director of the United States Patent and Trademark Office*